United States Patent [19]

Smith

[11] Patent Number: 5,353,112

[45] Date of Patent: Oct. 4, 1994

[54] OPTICAL INSPECTION METHOD AND APPARATUS

[75] Inventor: Martin P. Smith, Wargrave, United Kingdom

[73] Assignee: Gersan Establishment, Liechtenstein

[21] Appl. No.: 859,497

[22] PCT Filed: Jan. 25, 1991

[86] PCT No.: PCT/GB91/00109

§ 371 Date: Jun. 15, 1992

§ 102(e) Date: Jun. 15, 1992

[87] PCT Pub. No.: WO91/11699

PCT Pub. Date: Aug. 8, 1991

[30] Foreign Application Priority Data

Jan. 25, 1990 [GB] United Kingdom ............ 9001701.3

[51] Int. Cl.$^5$ .............................................. G01N 21/01
[52] U.S. Cl. ........................................ 356/244; 356/36; 356/243; 250/304
[58] Field of Search ................ 356/244, 246, 243, 237, 356/36-38, 445, 446, 375, 440; 250/252.1 A, 304, 561, 576

[56] References Cited

U.S. PATENT DOCUMENTS

| | | | |
|---|---|---|---|
| 3,224,324 | 12/1965 | Coppock et al. | 356/445 |
| 3,998,090 | 12/1976 | Wislocki . | |
| 3,999,860 | 12/1976 | Demsky et al. | 356/244 |
| 4,037,970 | 7/1977 | Webster et al. | 356/446 |
| 4,289,402 | 9/1981 | Teubner | 356/244 |
| 4,586,818 | 5/1986 | Lohr . | |
| 4,616,508 | 10/1986 | Jörn . | |
| 4,730,933 | 3/1988 | Lohr . | |
| 4,761,552 | 8/1988 | Rosenthal | 356/243 |
| 4,801,804 | 1/1989 | Rosenthal | 356/243 |
| 4,976,540 | 12/1990 | Kitamura et al. | 356/445 |

FOREIGN PATENT DOCUMENTS 1375321 10/1964 France .
0173730 10/1984 Japan .

Primary Examiner—Richard A. Rosenberger
Assistant Examiner—Hoa Q. Pham
Attorney, Agent, or Firm—Kerkam, Stowell, Kondracki & Clarke

[57] ABSTRACT

Apparatus for optical inspection of particulate material such as diamond abrasive comprises a body (1), an open sample container (25) which can rise and fall in the body, a reference member (71) above the container, mounted in a removable compaction head (9) of which the height relative to the body is fixed, and an optical inspection head (11) mountable on the body in place of composition head. The container is raised into contact with the reference member so that the surface of the sample is levelled and placed at a predetermined height. The compaction head is then removed and replaced by the optical inspection head. Consequently, the sample surface is always presented to the optical inspection head in a predetermined relationship and in particular at a predetermined height.

17 Claims, 2 Drawing Sheets

OPTICAL INSPECTION METHOD AND APPARATUS

FIELD OF THE INVENTION

This invention relates to the optical inspection of samples of particulate material and in particular, the the preparation and presentation of such samples for optical inspection.

BACKGROUND OF THE INVENTION

Optical inspection can be used to determine properties of particulate material, for example colour and reflectivity. One particular application of optical quality measurement is in monitoring the cosmetic quality of synthetic diamond crystals that are to be used as abrasive material. In one known measurement system, a sample is placed in a pot, that is to say an open container, and the exposed surface of the material is inspected by a suitable optical measurement device. Usually, the sample surface is uneven, and its height relative to the measurement device is inconstant, depending on the size of the particles. In the case of saw diamond abrasive, even though each sample is taken from a specific size range, there is still a variation of size and shape of particles within the sample. The resulting uneven sample surface and variations in surface height relative to the measurement device materially reduce the accuracy and repeatability of the measurement results, and measurement on one sample may not be readily comparable with measurements on other samples.

SUMMARY OF THE INVENTION

An object of the present invention is to improve the repeatability and accuracy of optical inspection measurements on particulate material, and in particular to provide for improved presentation of samples for optical inspection.

According to one aspect of the invention there is provided a method of preparing a sample of particulate material comprising placing the said material in an open container, providing a reference surface at a predetermined position, moving the container thereby bringing an exposed surface of the particulate material therein into intimate contact with the reference surface, holding the container in the position thus defined, and removing the reference surface, thereby presenting said sample with an exposed surface which is substantially even and located at a predetermined position defined by said reference surface.

According to another aspect of the invention there is provided apparatus for the optical inspection of particulate material, comprising a support, an open sample container mounted for movement in height relative to the support, a reference member having an undersurface placed at a predetermined height relative to the support and such that the sample of particulate material previously placed in the container can be raised into contact of the said undersurface, and means for holding the container in the position defined by such contact, the reference member being movable away from the container at said position to permit subsequent optical inspection of the exposed surface of the sample at the said position.

According to yet another aspect of the invention there is provided an optical inspection apparatus for particulate material, comprising a body, a container movably supported in the body for containing a sample of said material, a reference member having a reference and compaction surface on its underside and locatable above the container with the said surface at a predetermined position, and means for moving the container containing a said sample towards the said member when the latter is so located, thereby urging a said sample against the said surface, and means for holding the container in the thus-defined position when the said member is removed, so as to leave a compacted and even sample surface exposed for optical inspection.

The reference member or reference surface is preferably used not only to define the position of the sample surface but also to compact the sample and level the sample surface. Accordingly the sample will normally be urged against the reference member under a certain amount of pressure.

In a preferred arrangement, respective carriers for optical inspection devices and for the reference member are interchangeably mountable on the body or support, the reference member being removed after the sample has been set in position, and being replaced by the optical devices, such that the position of the optical devices relative to the exposed sample surface is always a predetermined relation defined by the position of the reference member, and in particular, the height of the optical devices relative to the sample surface is always constant.

The present invention provides that the sample surface is alway presented at a consistent height, and further, that the sample surface is rendered even. Consequently, the accuracy and repeatability of the optical measurements are greatly improved.

BRIEF DESCRIPTION OF THE DRAWINGS

The invention will be further described with reference to the drawings, in which.

DETAILED DESCRIPTION OF THE PREFERRED EMBODIMENT

The illustrated apparatus comprises a cylindrical body 1, within the lower region of which is a coaxial vertical bore 3 opening into a coaxial chamber 5 in the upper region of the body. The chamber 5 is open at the top.

Figure 1:
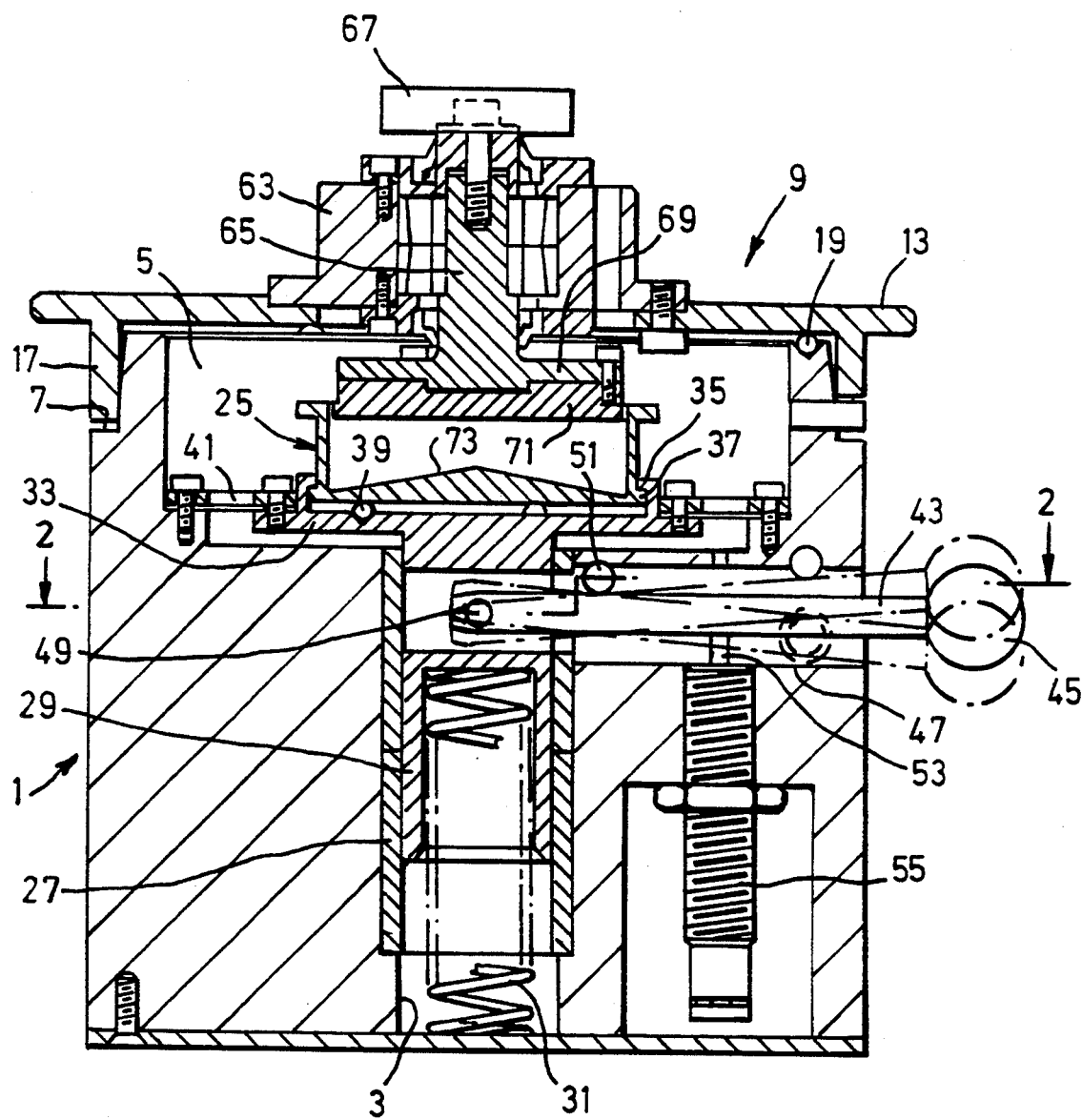
FIG. 1 shows the apparatus in section on a vertical diametral plane 1—1 of FIG. 2, with a sample-preparation or compaction head in position.
Figure 2:
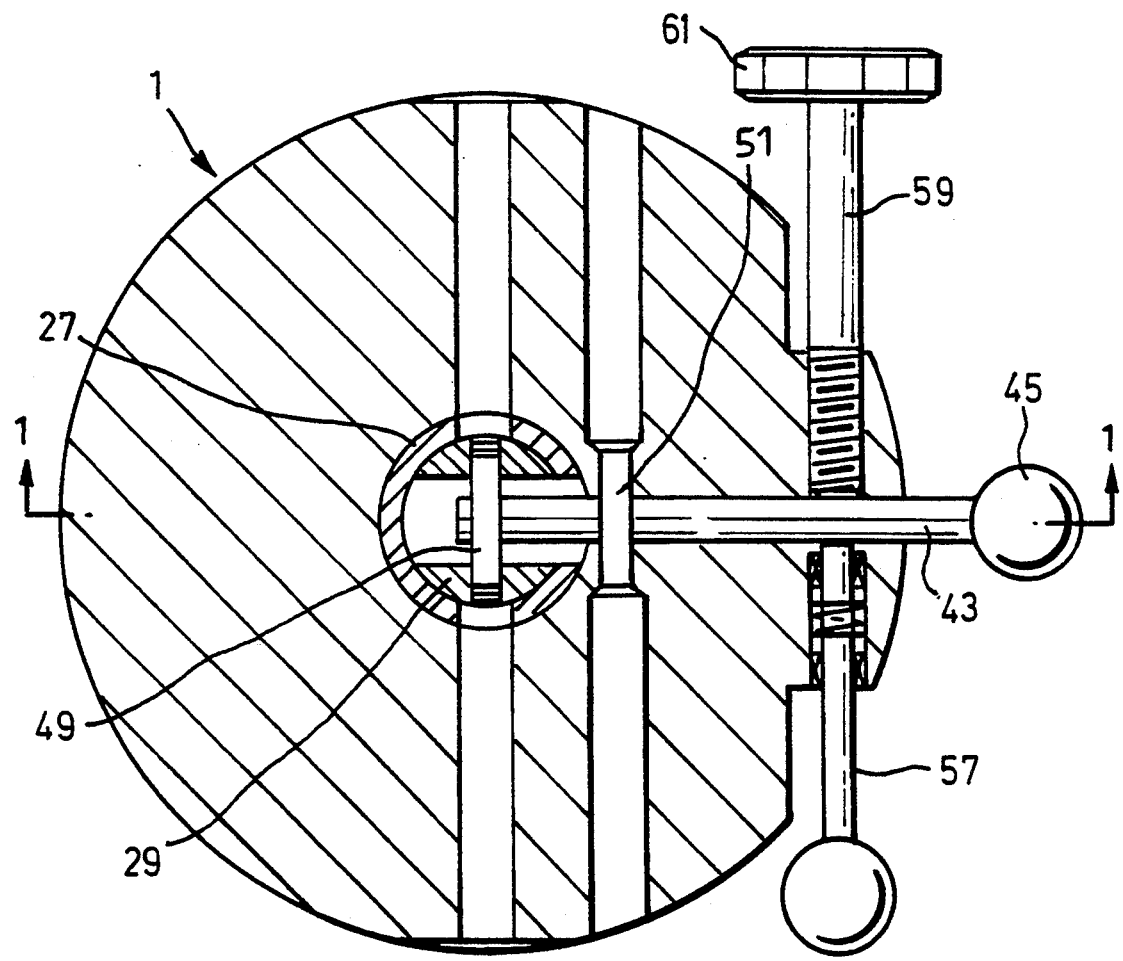
FIG. 2 is a section on the plane 2—2 of FIG. 1.
Figure 3:
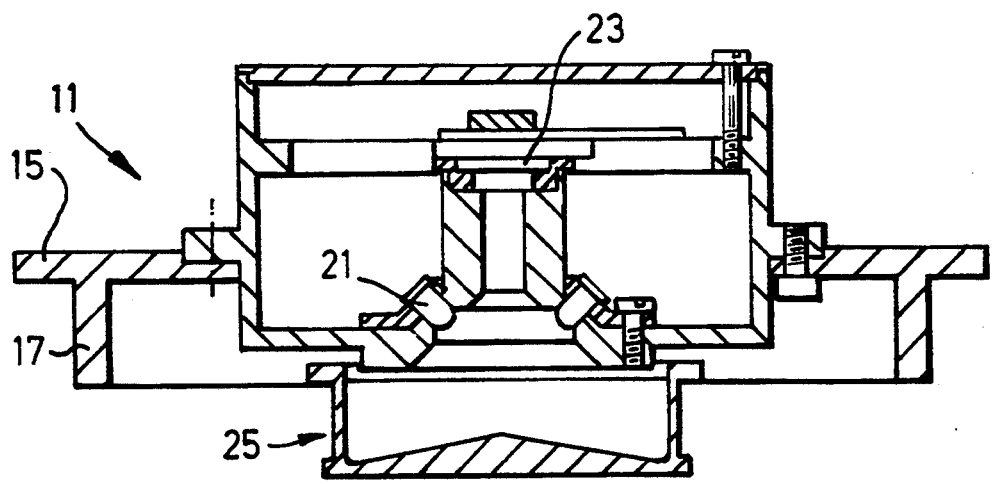
FIG. 3 shows an optical measurement head.

The upper end of the body has a peripheral rebate 7. On this upper end can be located a removable compaction head 9 as shown in FIG. 1, or a removable measurement head 11 as shown in FIG. 3.

Each of these heads comprises a circular cover or support plate, 13, 15, with a depending annular flange 17 which fits closely on the rebate 7. Seated in the annular uppermost surface of the body are three balls 19 placed at equal angular intervals about the vertical central axis of the body, forming a three-point seating for the cover plate 13 or 15. These balls, together with the interaction between the flanges 17 and the rebate 7, ensure that the compaction head, and the measurement head, are always seated on the body in precisely the same position, and in particular at the same height.

Each of these heads has a central aperture. Mounted in the central aperture of the measurement head 11 is a measurement unit comprising a ring of infra-red LEDs 21 each set at 45° to the central axis, and a detector 23 on the central axis, for optical inspection of a sample placed in a sample pot 25 in the chamber 5.

Infra red illumination is used for the reflectivity measurements owing to the fact that the samples may vary in colour. This colour should be neglected when making the measurement—by using the IR region of the spectrum all colours appear 'grey'. Thus there can be changes or mixed colours within the sample; this will not affect the measurement being made.

The precise nature of the optical measurement equipment provided will depend on the nature of the measurement required. For example, if colour changes are to be monitored, the light emitting devices may emit visible light. Suitable optical measurement equipment is well known and therefore this part of the apparatus will not be further described.

The means provided in the base for supporting the sample pot 25, and the compaction head 9, are designed to ensure that samples in the pot 25 are presented to the measurement head as consistently as possible, and in particular to ensure that the constituent particles in the sample are levelled and their exposed upper surface is always presented at the same height.

In the bore 3 is mounted a guide sleeve 27, within which is a vertically slidable plunger 29, urged upwards by a compression spring 31 seated in the base of the body.

At the upper end of the plunger 29 is a horizontal support plate 33 with an upstanding concentric annular flange 35 which forms a locating seat for the sample pot 25. The flange 35 has an in-turned lip with angularly spaced interruptions, and the base of the sample pot has correspondingly spaced lugs 37 which can be inserted through the interruptions in the lip and then engaged below the lip by rotation of the sample pot, in the manner of a bayonet connection. Seated in the upper surface of the plate 33 are three support balls 39 at equal angular intervals, which hold the lugs 37 in tight contact with the underside of the flange lip, thereby ensuring that the sample pot 25 cannot move vertically relative to the plunger 29.

The periphery of the plate 33 is connected to a shoulder in the base of the chamber 5 by an annular rubber sealing gasket 41, so that the upper region of the chamber 5 is sealed from its lower region and from the bore 3 and plunger 29, so that the plunger and associated components cannot be fouled by sample particles which may be spilled in the chamber 5.

A generally horizontal lever 43 with a handle 45 extends through a horizontal passage 47 in the body and is connected to the upper region of the plunger 29 by a horizontal pivot pin 49.

Adjacent the bore 3, the upper side of the lever rests against a horizontal fulcrum 51 in the upper region of the passage 47. On the opposite side of this fulcrum from the pivot pin 49, the lever rests on or is coupled to the piston rod 53 of a pneumatic damper cylinder or dashpot 55 mounted in the lower region of the body 1 with its axis vertical.

It will be seen that as the spring 31 urges the plunger 29 upwards, the outer region of the lever will pivot downwards about the fulcrum 51, pushing the piston rod 53 into the pneumatic cylinder 55, which accordingly damps the upward movement of the plunger 20 under the action of the spring. To lower the plunger 29, the handle 45 is raised manually. The cylinder 55 does not damp this movement.

The lever 43 can be locked in its raised position (with the plunger 29 lowered) by means of a spring-loaded locking pin 57 slidable in a bore in the body 1, at right angles to and intersecting the passage 47 in the lower region of the latter. When the lever 45 is fully raised, the pin can slide across the passage 47 below the lever, thereby locking the lever in its raised position and the plunger 29 in its lowered or retracted position.

Coaxial with the locking pin 57 but on the opposite side of the passage 47 is a locking screw 59 screw-threaded in the body 1 and provided with an operating knob 61. With the plunger 29 raised and the lever 43 correspondingly lowered, the locking screw can be tightened against the side of the lever to lock it in any selected position, thereby locating the plunger at any selected height.

The compaction head 9 comprises a boss 63 in which is journaled a central vertical rotatable shank 65 projecting downwards so as to be located in the chamber 5 when the measurement head is seated on the body 1. At the upper end of the shank 65 is a hand wheel or knob 67 by which the shank can be rotated about its vertical axis. At the lower end of the shank is a transverse horizontal support plate 69, on the underside of which is removably fastened a carbide disc 71 with a plane horizontal lower surface. The shank and carbide disc are mounted in such a way that the lower surface of the carbide disc is always at a fixed predetermined distance below the lower surface of the cover plate 13 of the compaction head, and therefore at a fixed predetermined height in relation to the body 1. The mounting may provide for initial adjustment or subsequent correction of this vertical spacing, but in operation it is kept constant.

The carbide disc is coaxial with and fits closely within the sample pot 25.

The operation of the apparatus will be described in relation to the inspection of the cosmetic quality of synthetic diamond crystals, in particular saw diamond abrasive, with reference to the surface condition and internal characteristics such as the presence of metallic inclusions. Crystals that are clear or contain only slight metallic inclusions are graded as "high/top quality", those with a large number of inclusions are graded "low quality". The apparatus is required to give a numerical output grading the batch being examined according to quality.

Typically, saw diamond abrasive comprises particles in the size range 200 μm to 2 mm, with each batch containing a single size range. A sample is taken, for example of approximately 200 carats, and is placed in the sample pot 25. The sample pot is locked onto the support plate 33 with the latter held in its lowest position by means of the locking pin 57.

The compaction head 9 is then fitted on the base 1 and the locking pin 57 is released, permitting the spring 31 to raise the plunger 29 and with it the sample pot 25, against the damping action of the pneumatic cylinder 55.

The raising of the sample pot 25 brings the particle sample in it into contact with the underside of the carbide disc 71, compacting the particle sample against the carbide disc. It will be understood that, if necessary, means may be provided for holding the compaction head 9 down on the body 1, against the upward pressure exerted by the spring 31.

The pressure exerted by the spring 31 will compact the sample in the pot 25 and level the surface of the sample against the carbide disc. The locking screw is then tightened against the lever 43, to lock the lever and thereby the plunger 29 and sample pot 25 in position with the sample surface at a reference level defined by the underside of the carbide disc 71.

To ensure an even surface of the sample, the inner base surface 73 of the sample pot is not flat but is profiled, for example with a shallow conical profile as shown in FIG. 1. The shape of this base surface is determined experimentally to achieve the pressure profile within the sample to ensur upper surface of the sample.

Additionally, the carbide disc can be rotated by knob 67 to improve the compaction and levelling of sample.

It will be understood that the most appropriate profile of the sample pot bottom surface will to some extent depend on the size and nature of the particles being compacted.

With the sample pot thus locked in position and presenting the sample surface at the reference level defined by the carbide disc 71, the compaction head 9 is removed and a measurement head 11 is placed on the base 1. The emitters 21 and detector 23 then measure the surface reflectivity of the sample. This measurement may be recorded by a computer and compared with previously known calibration limits set on the machine. The measured reading can then be presented numerically and/or can be classified as indicating high or low quality material.

Because the surface of the sample, irrespective of particle size and sample size, is always presented at the same position in space with respect to the measurement devices, reliably repeatable measurement is possible.

To calibrate the unit and ensure that the dynamic measurement range of the system is sufficient to resolve the differences within the samples being examined the following procedure is adopted:

The sample pot is removed and the holder locked in its down position via the locking pin. A calibration disc of height such that when placed in the locked down position its surface would coincide with the position of the reference carbide disc, is placed in the machine. This disc is painted white so that the signal obtained from the measurement unit sets the top boundary for the high quality material. A similar black disc is used to define the lower boundary of the measurement. Hence the dynamic range is set.

If measurements are very close together the white and black discs are replaced by a second set with different reflectivities to redefine the Max and Min of the measurement range and thus stretch the separation of the closely contested samples.

While the invention has been described with particular reference to determining the cosmetic qualities of saw diamond abrasive, the invention is more generally applicable to other situations where particulate material is to be sampled and optically inspected or measured, for example in measuring the colour of other types of synthetic and natural diamond abrasives, cosmetic powders, and other materials.

I claim:

1. A method of preparing a sample of particulate material comprising the steps of placing said material in an open container, providing a reference surface at a predetermined position, moving said container thereby bringing an exposed surface of said particulate material therein into intimate contact with said reference surface, holding said container in the position thus defined, and removing said reference surface, thereby presenting said sample with an exposed surface which is substantially even and located at a predetermined position defined by said reference surface and optically inspecting said exposed surface of said particulate material disposed at said position by optical inspection means disposed in predetermined manner relative to said position.

2. The method as claimed in claim 1, wherein said particulate material is urged against said reference surface thereby compacting said particulate material.

3. Apparatus for the optical inspection of particulate material, comprising a support, an open sample container mounted for movement in height relative to said support, a reference member having an undersurface placed at a predetermined height relative to the support and such that a sample of particulate material previously placed in said container can be raised into contact with said undersurface, and means for holding said container in a position defined by such contact said reference member being moveable away from said container at said position to permit subsequent optical inspection of an exposed surface of the sample at said position.

4. Apparatus as claimed in claim 3, further including means for urging said container towards said reference member, for compacting said sample against said undersurface.

5. Apparatus as claimed in claim 4 in which said container has an internal bottom surface profiled to provide between it and said undersurface a pressure distribution adapted for levelling the upper surface of said sample.

6. Apparatus as claimed in claim 3, 4 or 5 in which the reference member is rotatable about a vertical axis for levelling the surface of the sample.

7. Apparatus as claimed in claim 6 further including optical inspection means disposed or disposable at a predetermined height relative to said position for inspecting said sample surface after removal of said reference number.

8. Apparatus as claimed in claim 3, 4, or 5 further including optical inspection means disposed or disposable at a predetermined height relative to said position for inspecting the sample surface after removal of said reference member.

9. Apparatus as claimed in claim 8 in which said reference member is mounted on a carrier which is removable from said support, said carrier and support being provided with cooperating locating means such that when the carrier is located on the support the reference member has its undersurface at a predetermined level, said apparatus further including a second carrier similarly disposable removably on said support and carrying optical inspection means arranged to inspect the sample surface when the second carrier is disposed on said support, whereby the sample surface is always presented to said optical inspection means in a predetermined relationship determined by said reference member.

10. An optical inspection apparatus for particulate material, comprising a body, a container movably supported in said body for containing a sample of said material, a reference member having a reference and compaction surface on its underside and locatable above said container with said surface at a predetermined position, and means for moving said container containing said sample towards said member when the latter is so located, thereby urging said sample against said reference surface, and means for holding said container in the thus-defined position when said member is removed, so as to leave a compacted and even sample surface exposed for optical inspection.

11. An optical inspection apparatus as claimed in claim 10, wherein said container is removably supported on a platform which has its lower portion in the form of a plunger slidably received in a vertical hole in said body.

12. An optical inspection apparatus as claimed in claim 11, wherein said platform is urged upwards by a spring acting between said plunger and a part of said body.

13. An optical inspection apparatus as claimed in claim 12, wherein the upward motion of the platform is subject to mechanical damping.

14. An optical inspection apparatus as claimed in any one of claims 10 to 13, wherein said container has a circular opening and a lower portion of said member providing said surface is circular and is arranged to close said container when said container is moved towards said member.

15. An optical inspection apparatus as claimed in claim 14, wherein said lower portion of said member providing said surface is rotatable about an axis perpendicular to said surface.

16. An optical inspection apparatus as claimed in claim 14 wherein the base of said container is shaped to provide an appropriate pressure profile within said sample when the latter is compacted so as to ensure an even sample surface.

17. An optical inspection apparatus as claimed in any one of claims 10, 11, 12 or 13, wherein the base of said container is shaped to provide an appropriate pressure profile within said sample when the latter is compacted so as to ensure an even sample surface.

* * * * *